United States Patent [19]

Lee et al.

[11] Patent Number: 5,015,588

[45] Date of Patent: May 14, 1991

[54] METHOD FOR THE DETECTION OF FACTOR XIII IN PLASMA

[75] Inventors: Kyung Lee; Manford K. Patterson, Jr.; Paul J. Birckbichler, all of Ardmore, Okla.

[73] Assignee: The Samuel Roberts Noble Foundation, Inc.

[21] Appl. No.: 114,630

[22] Filed: Oct. 29, 1987

[51] Int. Cl.$^5$ .......................................... G01N 33/573
[52] U.S. Cl. ..................................... 436/69; 436/175; 436/178; 436/528; 435/7.5; 435/13
[58] Field of Search .................... 436/69, 518, 524, 56, 436/69, 166, 169, 175, 177, 178; 435/7, 13, 18

[56] References Cited

U.S. PATENT DOCUMENTS

| | | | |
|---|---|---|---|
| 4,228,237 | 10/1980 | Hevey et al. | 436/513 X |
| 4,601,977 | 7/1986 | Ogawa et al. | 435/13 |
| 4,812,395 | 3/1989 | Ballas et al. | 435/7 |

OTHER PUBLICATIONS

"Manual of Clinical Laboratory Immunology", 3rd ed., Rose et al., p. 106 (1986).
"Name Reactions in Organic Chemistry", Surrey, p. 215 (1961).
Rappuoli et al., "Competitive Enzyme Immunoassay for Human Chorionic Somatomammotropin Using the Avidin-Biotin System", Analytic Bioch., 118, 168–172 (1981).
Lorand, et al., "Diagnostic and Genetic Studies on Fibrin-Stabilizing Factor with a New Assay Based on Amine Incorporation", 48, *J. Clinical Investigation* 1054 (1969).
Curtis, et al., "Fibrin-Stabilizing Factor (Factor XIII)", in 45 *Methods and Enzymology* 177–191 (1976).
Folk et al., "Transglutaminases", in 113 *Methods and Enzymology* 358, 364 (1985).
Miraglia, et al., "Measurement of Blood Coagulation Factor XIIIs Formation in Plasma Containing Glycyl-L-prolyl-arginyl-L-proline", 144 *Analytical Biochemistry* 165–171 (1985).
Lorand et al., "New Colored and Fluorescent Amine Substrates for Activated Fibrin Stabilizing Factor (Factor XIIIa) and for Transglutaminase", 131, *Analytical Biochemistry* 419–425 (1983).
Muszbek, et al., "Kinetic Determination of Blood Coagulation Factor XIII in Plasma", 31, *Clinical Chemistry* 35–40 (1985).
Takagi, et al., "Modification of Transglutaminase Assay: Use of Ammonium Sulfate to Stop the Reaction", 153, *Analytical Biochemistry* 295–298 (1986).
Lorand et al., "Amine Specificity in Transpeptidation. Inhibition of Fibrin Cross-Linking", 7 *Biochemistry* 1214 (1968).
Lee, et al., "Development of Selective Inhibitors of Transglutaminase", 260, *J. of Biological Chemistry* 14689 (1985).
Lorand et al., "A Filter Paper Assay for Transamidating Enzymes Using Radioactive Amine Substrates", 50 *Analytical Biochemistry* 623–631 (1972).
Lorand et al., "Transamidating Enzymes II. A Continuous Fluorescent Method Suited for Automating Measurements of Factor XII in Plasma", 44 *Analytical Biochemistry* 221–231 (1971).

*Primary Examiner*—David L. Lacey
*Assistant Examiner*—Jeffrey R. Snay
*Attorney, Agent, or Firm*—Richards, Medlock & Andrews

[57] ABSTRACT

An assay method for the detection of Factor XIII in plasma is disclosed in which a primary amine derivative of biotin such as preferably 5-(biotinamido) pentylamine is incubated with a glutamine substrate and activated Factor XIII (Factor XIIIa) to form a biotinylated product which may be measured by convention detection assays. In a preferred embodiment, the biotinylated product is bound to a well in a microtiter plate or other solid support and the product is measured by a colorimetric assay which may be read by an automated spectrophotometric plate reader.

9 Claims, 3 Drawing Sheets

METHOD FOR THE DETECTION OF FACTOR XIII IN PLASMA

TECHNICAL FIELD

This invention relates to methodology for detecting and quantitating blood coagulation Factor XIII.

BACKGROUND OF THE INVENTION

Factor XIII (FX III) is a zymogen in blood plasma that is transformed into its active form (FXIIIa) by thrombin and $Ca^{2+}$. FXIIIa [also called activated fibrin-stabilizing factor, fibrinoligase, or plasma transglutaminase, EC 2.3.2.13(R-glutaminylpeptide:amine γ-glutamyltransferase)] is the last enzyme generated in the blood coagulation cascade and catalyzes the formation of intermolecular γ-glutamyl-ε-lysine crosslinks between fibrin molecules, thereby stabilizing the fibrin clot structure and conferring resistance to fibrinolysis. The crosslink formation by FXIIIa is important for normal blood coagulation and wound healing, and possibly in pathologic conditions such as thrombosis, atherosclerosis, and tumor growth and metastasis.

For clinical and basic studies on FXIII, a number of assays have been developed for measuring enzyme activity generated after treatment of the inactive zymogen with thrombin and $Ca^{2+}$.

Lorand et al., "Diagnostic and Genetic Studies on Fibrin-Stabilizing Factor with a New Assay Based on Amine Incorporation," 48 *J. Clinical Investigation* 1054 (1969) have described an assay in which fibrinoligase catalyzes the incorporation of a fluorescent amine, monodansylcadaverine into casein. A fluorimetric method is then employed to analyze the reaction product. Curtis et al., "Fibrin-Stabilizing Factor (Factor XIII)" in 45 *Methods in Enzymology* 177-191 (1976), describe several methods for assaying Factor XIII including an assay utilizing the incorporation of dansylcadaverine into casein followed by measuring protein-bound fluorescence, a continuous rate assay for measuring enzymic incorporation of a fluorescent amine into a protein acceptor, a filter paper assay for measuring enzymic incorporation of radioactively labeled amines into proteins, a continuous rate assay for measuring the production of free thiol, and a continuous rate assay for measuring water-insoluble fluorescent amide. Folk et al., "Transglutaminases" in 113 *Methods in Enzymology* 358, 364 (1982), describe an assay which measures incorporation of radiolabeled putrescine into a casein mixture. Miraglia et al., 144 *Analytical Biochemistry* 165-171 (1985) describe Factor XIIIa measurement by incorporation of [³H] putrescine into casein. Lorand et al., 131 *Analytical Biochemistry* 419 (1983), describe three (two fluorescent and one colored) derivatives of cadaverine which could serve as substrates for fibrinoligase (FXIIIa). Fluorescent and colorimetric techniques for measuring Factor XIII are described. Muszbek et al., 31 *Clinical Chemistry* 35-40 (1985), describe a kinetic assay for determination of Factor XIII in plasma. The release of ammonia in the FXIIIa reaction with a modified β-casein is continuously monitored with an indicator reaction. U.S. Pat. No. 4,601,977 to Ogawa et al. "Method for Measuring the Activity of Plasma Factor XIII" (July 22, 1986) describes a method using incorporation of a fluorescent cadaverine derivative into casein, followed by use of a column gel for separating reacted cadaverine derivative from unreacted cadaverine derivative.

Despite the numerous methodologies described, there has been a continuing need for a simple assay procedure which is suitable for routine analysis for Factor XIII in the diagnostic laboratory.

SUMMARY OF THE INVENTION

An assay for the detection of Factor XIII is now described which employs a primary amine derivative of biotin for incorporation into a glutamine substrate to for a biotinylated reaction product. This incorporation is catalyzed by the active zymogen FXIIIa, which is formed by incubating thrombin and $Ca^{2+}$ with plasma containing FXIII. The active FXIII (FXIIIa) catalyzes the incorporation of the primary amine into N,N-dimethylcasein or other glutamine substrate resulting in a biotinylated product. The biotinylated product may then be quantitated by any suitable procedure, preferably a colorimetric procedure.

The primary amine derivative of biotin is preferably of one of the following general formulas:

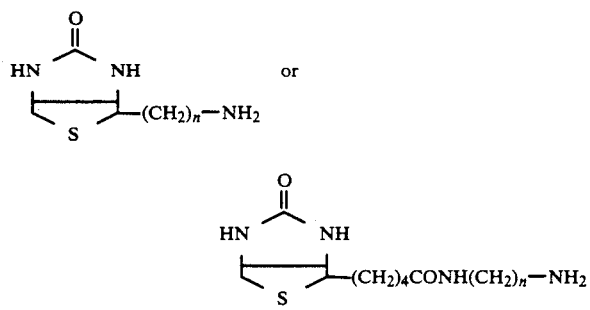

where n = 1, 2, 3 . . . n

Preferably, n=4, 5 or 6. Most preferably, n=5. However, other primary amine derivatives of biotin may also work.

In one aspect of the invention, a primary amine derivative of biotin is reacted with a glutamine substrate and an activated plasma sample to form a biotinylated reaction product which is then quantified by any appropriate method.

In another aspect of the invention, a solid support is employed to which the formed biotinylated product is bound. The reactants are then washed away and the detection assay for the biotinylated products bound to the solid support may be performed. In a preferred embodiment of the invention, a microtiter plate is utilized, each well serving as a solid support, for binding to the biotinylated product. Once the biotinylated product is bound, a colorimetric assay is utilized to quantify the reaction product. Preferably, a colorimetric assay utilizing streptavidin-β-galactosidase and p-nitrophenyl-β-D-galactopyranoside (PNPG) as a detector for the biotinylated product bound to the well is employed. A colored product, p-nitrophenol, is produced and measured by spectrophotometric absorbance at 405 nm.

In a further aspect of the invention, the method is utilized to assay for Factor XIII that is activated to Factor XIIIa through any appropriate method. The reaction product of a primary amine derivative of biotin and a glutamine substrate is then analyzed.

DETAILED DESCRIPTION OF THE INVENTION

This invention comprises a novel method for detecting Factor XIII.

Blood specimens are collected and platelet-poor plasma prepared. The blood sample may be citrated by admixture with a 3.8% sodium citrate solution. The platelet-poor plasma may be prepared by centrifuging a blood specimen at 2500×g for 10 minutes or by other suitable techniques. The plasma may be stored frozen at −70° C. until analysis. Analysis of non-frozen samples is preferably performed within about 8 hours of collecting the blood specimen, however any specimen retaining Factor XIII enzymatic activity may be analyzed.

A plasma sample to be assayed for Factor XIII first must be treated to remove or desensitize intrinsic fibrinogen in the plasma in order to prevent clotting of the plasma and to eliminate fibrin from the assay which could compete with the glutamine substrate. This step may be performed by any appropriate method for eliminating the fibrinogen influence, such as those described by Lorand et al., 48 *J. Clinical Investigation* 1054–1064 (1969) or Muszbek et al., 31 *Clinical Chemistry* 35–40 (1985). Preferably, defibrination by bentonite treatment (40 mg/ml plasma) is employed. Citrated plasma is mixed with 40 mg/ml bentonite. The mixture is incubated with rocking for 10 minutes, then centrifuged at 8740×g for 1 minute to remove fibrinogen. The supernatants are collected as a defibrinated, plasma sample. Fibrogen-free examples may be assayed directly.

Figure 1:
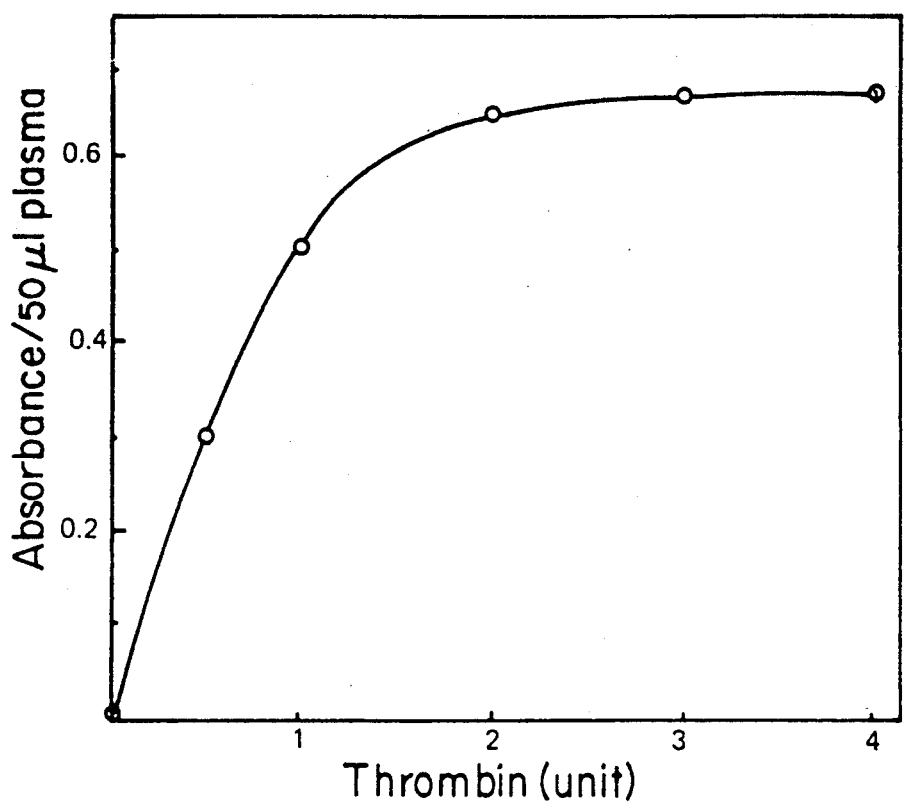
FIG. 1 shows the dependence of FXIIIa activity on the concentration of thrombin used for activating (20 min) FXIII in 50 μl of bentonite-treated plasma.
Figure 2:
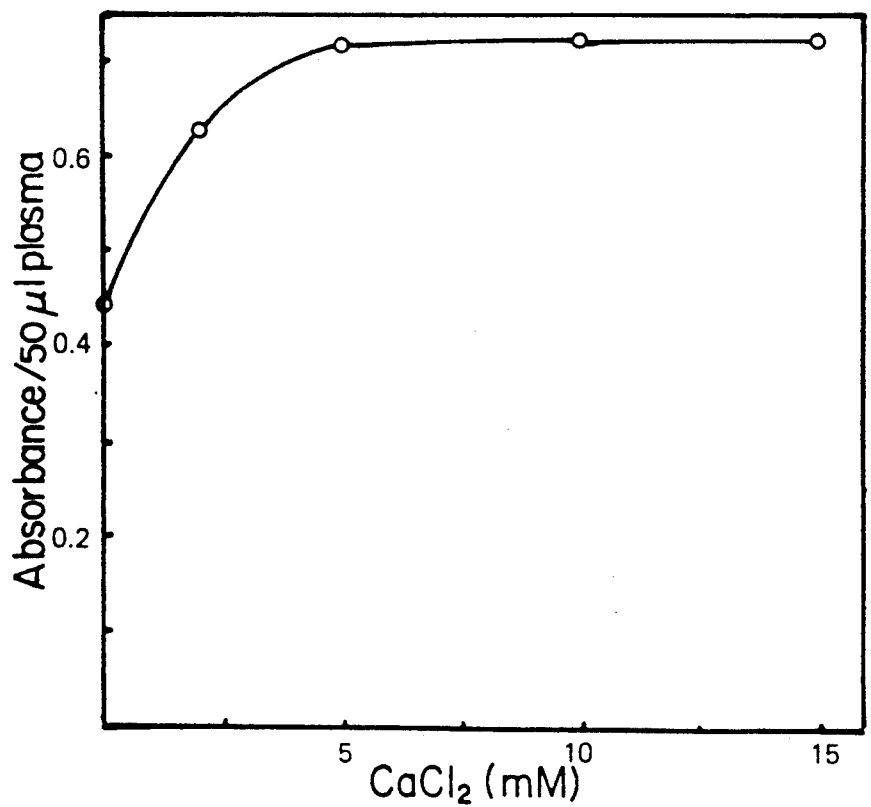
FIG. 2 shows the dependence of FXIIIa activity on calcium ion concentration.

The FXIII in the defibrinated plasma sample is then activated to FXIIIa by incubation with thrombin and $Ca^{2+}$. The resulting plasma sample is herein referred to as an activated plasma sample. In the activation, an appropriate amount of thrombin to employ is greater than 2 NIH units per 50 microliters of defibrinated plasma sample. Preferably, 2.5 NIH units per 50 microliters of defibrinated plasma will be employed. FIG. 1 depicts the dependence of FXIIIa activity on the concentration of thrombin used in the activation step. A standard curve such as depicted in FIG. 1 may be prepared to ascertain the appropriate amount of thrombin to use to achieve maximum activation under altered conditions. The preferred concentration of $Ca^{2+}$ to add is about 5 mM, but may be chosen according to an assay plotting dependence of FXIIIa activity on $Ca^{2+}$ concentration, shown in FIG. 2. Endogenous $Ca^{2+}$ may eliminate the necessity of adding $Ca^{2+}$ in some instances.

The thrombin activation step results in formation of FXIIIa, a two-substrate enzyme which catalyzes an amine substrate incorporation into a glutamine substrate. Any primary amine derivative of biotin may be used as the amine substrate. Preferably, the amine substrate is of the general formula

Figure 3:
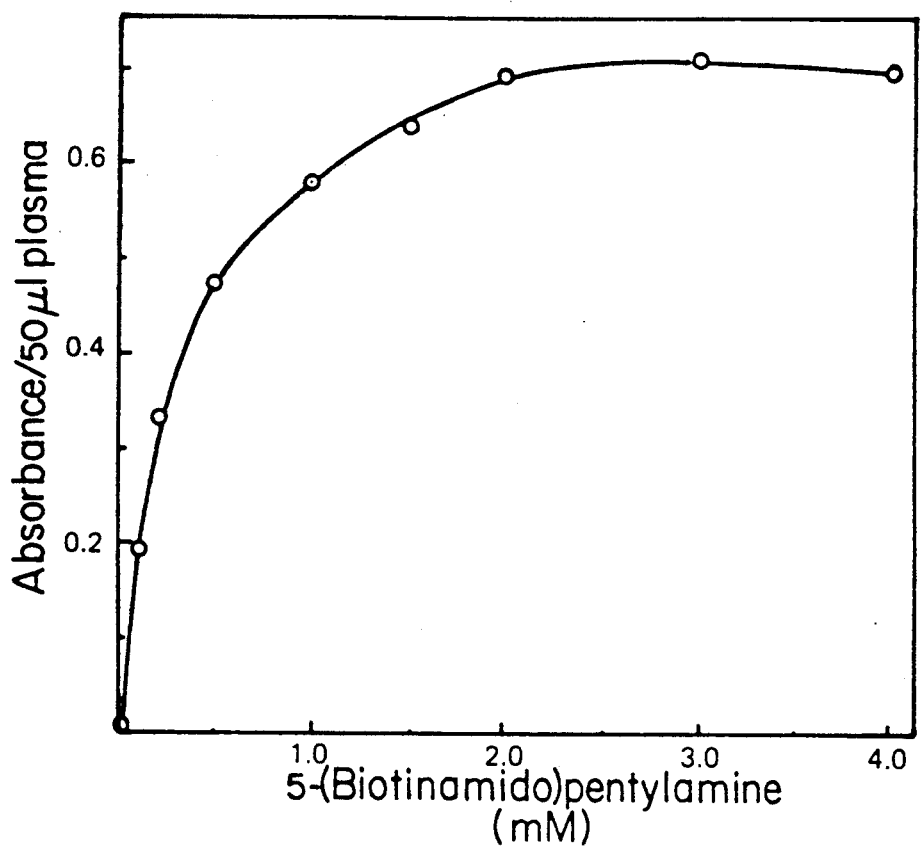
FIG 3 shows the dependence of FXIIIa activity on 5-(biotinamido)pentylamine concentration.

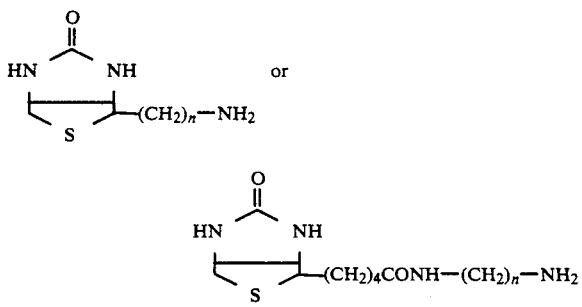

where n=1, 2, 3, . . . n. Preferably, n=4, 5 or 6. Most preferably, n=5. A novel, biotin-labeled amine substrate, 5-(biotinamido)-pentylamine, was designed by us for this assay and synthesized for us by E. K. Fujimoto, Pierce Chemical Co., Rockford, Ill. This substrate was designed with the objective of optimizing the activity of the enzyme on the reaction. FIG. 3 depicts the relationship between the concentration of 5-(biotinamido)-pentylamine and the activity of FXIIIa. The amine substrate may be employed in excess of about 2 mM. The preferred concentration is 2.5 mM.

An appropriate glutamine substrate is chosen for the reaction. This substrate may be chosen from selected proteins or peptides containing glutamine residue(s) such as casein, insulin, fibronectin, fibrin, tubulin, vimentin and others. Most preferred is N,N-dimethylcasein since the $\epsilon$-amino group of lysine is N-methylated to prevent the formation of intermolecular crosslinks between glutamine and lysine residues of the casein molecules. The amount of glutamine substrate to use is preferably at the level to allow near maximum velocity of amine incorporation and is determined by plotting concentration of glutamine substrate against activity, or a parameter correlating with activity. There may be some endogenous glutamine substrate in the plasma. The preferred concentration of N,N-dimethylcasein is 1.0 mg/ml.

The amine substrate, the glutamine substrate, and Factor XIIIa are then reacted, in an appropriate reaction vessel such as a microtiter plate well. The preferred reaction time is between 10 minutes and 60 minutes. Forty minutes is preferred. The reaction is terminated by addition of 20 mM EDTA.

Subsequent to termination of the reaction, the biotinylated product may be analyzed by any appropriate detection assay.

Preferably, the biotinylated product is immobilized on a solid support such as, for example, a microtiter plate, beads, or nitrocellulose discs. Most preferably, a microtiter plate is utilized by transferring an aliquot of the reaction mixture liquid to a clean microtiter well and incubating with shaking for a sufficient period to allow binding (about one hour). The liquid is then removed from the well and the well washed about three times with an appropriate washing solution. After washing, the bound biotinylated product is assayed. A preferable assay is colorimetric. One effective colorimetric assay is performed by adding a streptavidin-$\beta$-galactosidase solution to the, wells, and incubating. p-nitrophenyl-$\beta$-D-galactopyranoside (PNPG) is then added and incubated. The absorbance at 405 nm of the resulting colored product, p-nitrophenol, can then be determined and correlated to concentration of the biotinylated product. A plate reader is preferably utilized to automate the process.

EXAMPLE 1

A. Equipment

Microelisa Auto Plate Reader (Model MR580, Dynatech Laboratories, Alexandria, VA) was used to quantify results of the colorimetric FXIII assay, and an Orbit Shaker (Model 3520, Lab-Line Instruments, Melrose Park, Ill.) was used to agitate microtiter plates containing reaction mixtures.

B. Plasma Samples and Other

Blood specimens, collected in Vacutainer tubes (Becton Dickinson, Rutherford, NJ) containing 3.8% sodium citrate solutions, were obtained from the Clinical Laboratory of Memorial Hospital of Southern Oklahoma. Platelet-poor plasma was prepared within 48 hours of collection by centrifuging at 2500×g for 10 minutes. For best results, the plasma samples were analyzed within 8 hr. of collecting or stored frozen at −70° C. Factor XIII-deficient plasma was purchased from Sigma Chemical Co., St. Louis, Mo., and 96-well polyvinyl microtiter plates from Becton Dickinson Labware, Oxnard, Calif.

C. Reagents

Bentonite powder (Sigma).

Human thrombin (1000 NIH units/mg, Sigma) was used to activate plasma Factor XIII: 1000 NIH units in a vial were reconstituted in 4 ml of 25% aqueous glycerol, pH 7.4.

Tris-buffered saline (TBS) (40 mM Tris-HCl, pH 8.3, containing 150 mM NaCl)

N,N-dimethylcasein (Calbiochem, La Jolla, Calif.), 10 mg/ml in TBS containing 50 mM dithiothreitol.

5-(Biotinamido)pentylamine (synthesized for us by E. K. Fujimoto, Pierce Chemical Co., Rockford, Ill.), 5 mM, in TBS.

$CaCl_2$ (Sigma), 50 mM, in TBS.

Ethylenediaminetetraacetic acid (EDTA) (Sigma), 200 mM, in TBS.

All the above reagents are stored at −20° C.

Washing solution, pH 7.4, phosphate buffered saline (Sigma) containing 2.0 mM 2-mercaptoethanol, 0.05% Tween-20, and 0.05% sodium azide.

Streptavidin-$\beta$-galactosidase (Bethesda Research Labs, Gaithersburg, Md.), freshly prepared at 1:1000 dilution in washing solution.

p-nitrophenyl-$\beta$-D-galactopyranoside (PNPG) (Bethesda Research Labs), freshly prepared at 1 mg/ml in 50 mM $Na_2HPO_4$-HCl, pH7.2 containing 1.5 mM $MgCl_2$.

D. Procedure

All assay steps were carried out at room temperature. Citrated plasma was mixed with bentonite (40 mg/ml plasma) and incubated with, rocking for 10 minutes, and centrifuged in an Eppendorf microcentrifuge at 8740×g, for 1 minute to remove fibrinogen from the plasma. The fibrinogen-free supernatants (50 μl) were dispensed in wells of a microtiter plate, and incubated with shaking on an orbit shaker for 20 minutes after 10 μl of thrombin was added. Then, 20 μl of $CaCl_2$ solution, 20 μl of dimethylcasein solution, and 100 μl of 5-(biotinamido) pentylamine solution were dispensed in the wells. For controls, $CaCl_2$ was replaced by 20 μl of EDTA solution. The reaction mixture was incubated with shaking for 40 minutes. The reaction was terminated by the addition of 20 μl of EDTA solution.

For immobilizing the FXIIIa-catalyzed reaction products on the microtiter plate, 200 μl of the reaction mixture was transferred to other microtiter wells and incubated with shaking for 60 minutes. The liquid was removed and the wells washed three times with washing solution. To each well, 150 μl of streptavidin-$\beta$-galactosidase solution were added and incubated with shaking for 30 minutes. Absorbance at 405 nm was read on a Dynatech plate reader 20 minutes after the addition of PNPG and the value used as a measure of FXIIIa activity.

Figure 4:
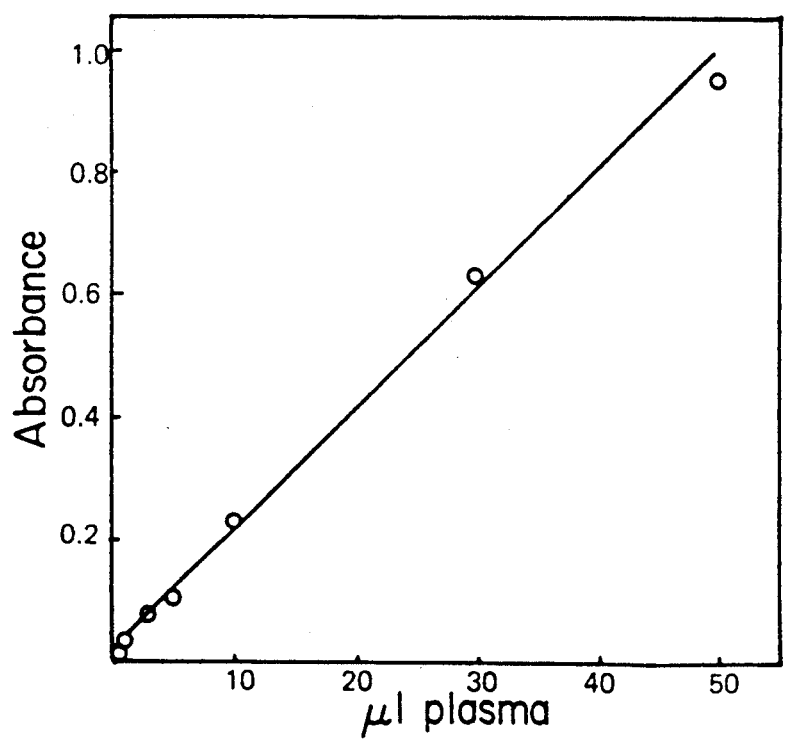
FIG. 4 shows the linear relationship between FXIIIa activity and the concentration of plasma employed in the assay described in Example 1.

A linear relationship between the FXIIIa activity and the concentration of plasma employed in the assay was found. (FIG. 4). Plasma dilutions were made with FXIII—efficient plasma which had no detectable FXIIIa activity, either by the assay described herein, or by the radiometric filter paper method described by Lorand et al., 50 *Analytical Biochemistry* 623–631 (1972).

EXAMPLE 2

Figure 5:
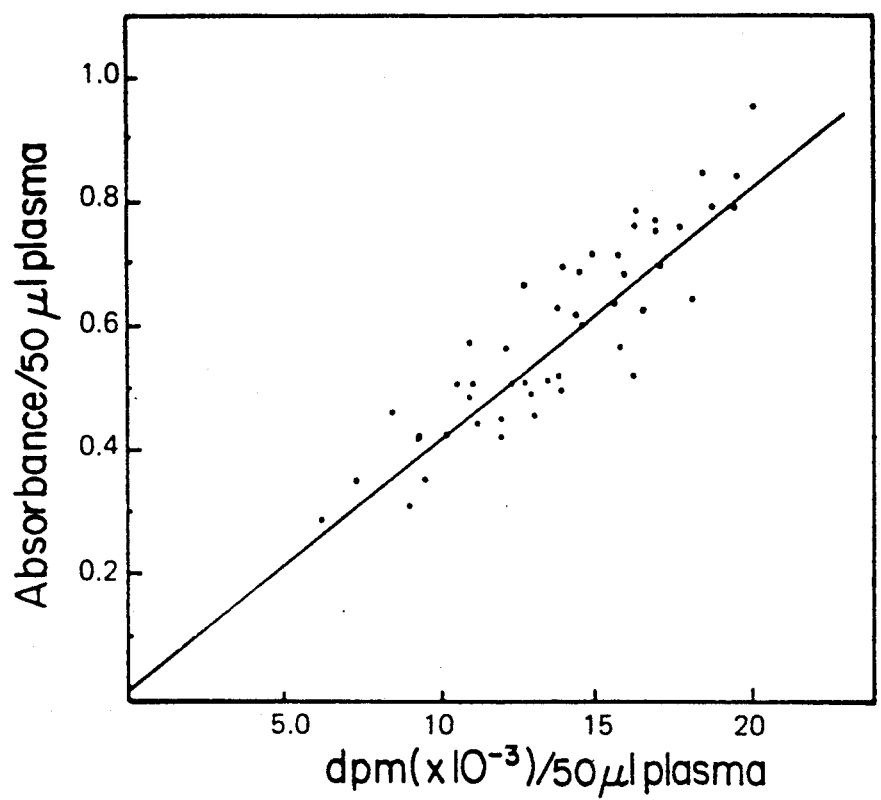
FIG. 5 shows the correlation between FXIIIa activity determined by the radiometric filter paper assay (abscissa) and by the new method (ordinate) as detailed in Example 2.

47 human plasma samples were assayed for FXIII activity by the method described in Example 1 and were also assayed using the radiometric filter paper assay described by Lorand, et al, 50 *Analytical Biochemistry*, 623–631 (1972). FIG. 5 shows the correlation between the two methods. The linear equation describing the results is $y = 4.1 \times 10^{-5}x + 0.022$ and the correlation coefficient $\gamma = 0.917$.

We claim:

1. A method for quantitating blood coagulation Factor XIII in a plasma sample, comprising the steps of:
   (a) desensitizing or removing intrinsic fibrinogen from the plasma sample to form a defibrinated plasma sample;
   (b) incubating said defibrinated plasma sample with thrombin and $Ca^{2+}$ to activate Factor XIII to Factor XIIIa in said defibrinated plasma sample, thereby forming an activated plasma sample;
   (c) incubating said activated plasma sample with a glutamine substrate and a primary amine derivative of biotin to form a biotinylated reaction product; and
   (d) quantitating said biotinylated reaction product wherein said primary amine derivative of biotin is a compound of the general formula

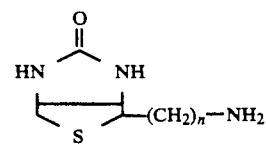

wherein n = 1, 2, 3, 4, 5, or 6.

2. A method according to claim 1, where N = 4, 5 or 6.

3. A method according to claim 2, where n = 5.

4. A method for quantitating blood coagulation Factor XIII in a plasma sample, comprising the steps of:
   (a) desensitizing or removing intrinsic fibrinogen from the plasma sample to form a defibrinated plasma sample;
   (b) incubating said defibrinated plasma sample with thrombin and $Ca^{2+}$ to activate Factor XIII to Factor XIIIa in said defibrinated plasma sample, thereby forming an activated plasma sample;

(c) incubating said activated plasma sample with a glutamine substrate and a primary amine derivative of biotin to form a biotinylated reaction product;

(d) binding said biotinylated reaction product to a solid support;

(e) washing said solid support to remove reactants while leaving said biotinylated reaction product bound thereto; and (f) quantitating said bound biotinylated reaction product on said solid support wherein said primary amine derivative of biotin is a compound of the general formula

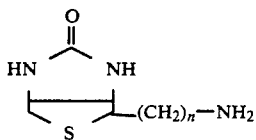

where n = 1, 2, 3, 4, 5, or 6.

5. A method according to claim 4, wherein n = 4, 5 or 6.

6. A method according to claim 5, where n = 5.

7. A method for assaying Factor XIII, comprising the steps of:

(a) activating a fibrinogen-free sample of Factor XIII to form Factor XIIIa;

(b) incubating said Factor XIIIa with a glutamine substrate and a primary amine derivative of biotin to form a biotinylated reaction product; and (c) quantitating said biotinylated reaction product wherein said primary amine derivative of biotin is a compound of the general formula

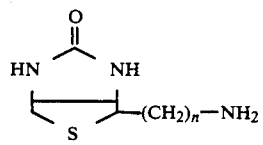

where n = 1, 2, 3, 4, 5, or 6.

8. A method according to claim 7, where n = 4, 5 or 6.

9. A method according to claim 8, where n = 5.

* * * * *